United States Patent
Kaus et al.

(10) Patent No.: US 7,596,207 B2
(45) Date of Patent: Sep. 29, 2009

(54) METHOD OF ACCOUNTING FOR TUMOR MOTION IN RADIOTHERAPY TREATMENT

(75) Inventors: Michael Kaus, Hamburg (DE); Vladimir Pekar, Hamburg (DE); Todd Mcnutt, Verona, WI (US)

(73) Assignee: Koninklijke Philips Electronics N.V., Eindhoven (NL)

(*) Notice: Subject to any disclaimer, the term of this patent is extended or adjusted under 35 U.S.C. 154(b) by 18 days.

(21) Appl. No.: 11/995,337

(22) PCT Filed: Jul. 10, 2006

(86) PCT No.: PCT/IB2006/052332
§ 371 (c)(1),
(2), (4) Date: Jan. 11, 2008

(87) PCT Pub. No.: WO2007/007276
PCT Pub. Date: Jan. 18, 2007

(65) Prior Publication Data
US 2008/0219406 A1    Sep. 11, 2008

Related U.S. Application Data

(60) Provisional application No. 60/595,551, filed on Jul. 14, 2005.

(51) Int. Cl.
*A61N 5/10* (2006.01)
*G01N 23/04* (2006.01)
(52) U.S. Cl. .......................... 378/65; 378/62
(58) Field of Classification Search ............. 378/62–65
See application file for complete search history.

(56) References Cited

U.S. PATENT DOCUMENTS

| 6,661,870 | B2 * | 12/2003 | Kapatoes et al. ............. 378/65 |
| 6,766,043 | B2 * | 7/2004 | Zeng et al. .................. 382/128 |
| 2002/0122530 | A1 | 9/2002 | Erbel et al. |
| 2004/0133102 | A1 * | 7/2004 | Uematsu ..................... 600/436 |
| 2004/0184647 | A1 | 9/2004 | Reeves et al. |
| 2004/0242987 | A1 | 12/2004 | Liew et al. |
| 2004/0254448 | A1 | 12/2004 | Amies et al. |
| 2005/0251029 | A1 | 11/2005 | Khamene et al. |
| 2008/0212852 | A1 * | 9/2008 | Sun et al. .................... 382/128 |

FOREIGN PATENT DOCUMENTS

WO   2004004829 A1   1/2004

(Continued)

OTHER PUBLICATIONS

Christensen, G. E., et al.; Image-Based Dose Planning of Intracavitary Brachytherapy: Registration of Serial-Imaging Studies Using Deformable Anatomic 2001; Int. J. Radiation Oncology Biol. Phys.; 51(1)227-243.

(Continued)

*Primary Examiner*—Irakli Kiknadze

(57) ABSTRACT

A method and apparatus accounting for tumor motion during radiation therapy is provided. The method allows for radiation therapy treatments based on updated radiation therapy plans. For each fractionate radiation treatment that results in an updated radiation treatment, radiation treatment images are acquired, automatically segmented, and then subject to deformable registration to develop updated contours and an updated radiation therapy plan.

15 Claims, 2 Drawing Sheets

FOREIGN PATENT DOCUMENTS

| | | |
|---|---|---|
| WO | 2004046995 A2 | 6/2004 |
| WO | 2005031629 A1 | 9/2004 |
| WO | 2004111936 A1 | 12/2004 |
| WO | 2004111937 A1 | 12/2004 |

OTHER PUBLICATIONS

Christensen, G. E., et al.; Volumetric Transformation of Brain Anatomy; 1997; IEEE Trans. on Medical Imaging; 16 (6)864-877.

Fornefett, M., et al.; Radial basis functions with compact support for elastic registration of medical images; 2001; Image and Vision Computing; 19:87-96.

Hill, D.L.G., et al.; Medical image registration; 2001; Phys. Med. Biol.; 46:R1-R45.

Joshi, S., et al.; Multiscale Deformable Model Segmentation and Statistical Shape Analysis Using Medial Descriptions; 2002; IEEE Trans. on Medical Imaging; 21(5)538-550.

Kabus, S., et al.; B-Spline Registration of 3D Images with Levenberg-Marquardt Optimization; 2004; Medical Imaging; 304-313.

Kaus, M. R., et al.; Estimation of organ motion from 4D CT for 4D radiation therapy planning of lung cancer; 2004; Medical Image Computing and Computer-Assisted Intervention; vol. 2; abstract.

Keall, P.; 4-Dimensional Computed Tomography Imaging and Treatment Planning; 2004; Seminars in Radiation Oncology; 14(1)81-90.

Mcinerney, T., et al.; Deformable Models in Medical Image Analysis: A Survey; 1996; Medical Image Analysis; 1(2) 91-108.

Montagnat, J., et al.; Volumetric Medical Images Segmentation using Shape Constrained Deformable Models; http://www.lirmm.fr/manifs./UEE/docs/delingette/pdf/cvrmed.pdf May 8, 2005.

NSF Engineering Research Center for Subsurface Sensing & Image Systems http://www.censsis.neu.edu/seminars/2004/broysam_051304.pdf May 8, 2005.

Rueckert, D.; Nonrigid Registration: Concepts, Algorithms, and Applications; 2001; CRC Press LLC; 281-301.

Wiemker, R., et al.; Optimal Thresholding for 3D Segmentation of Pulmonary Nodules in High Resolution CT; 2001; Elsevier Science B.V.; 611-616.

Yan, D., et al.; Adaptive radiation therapy; 1997; Phys. Med. Biol.; 42:123-132.

\* cited by examiner

METHOD OF ACCOUNTING FOR TUMOR MOTION IN RADIOTHERAPY TREATMENT

CROSS REFERENCE TO RELATED APPLICATIONS

This application claims the benefit of U.S. provisional application Ser. No. 60/595,551 filed Jul. 14, 2005, which is incorporated herein by reference.

DESCRIPTION

Radiotherapy is the treatment of diseases, such as cancer tumors, with radiation, such as X-ray radiation. In the course of administering radiation to the diseased tissue, some healthy tissue is also exposed to the radiation. Exposure of healthy tissue to radiation can cause treatment-related complications. As such, it is desirable to accurately and precisely contour the diseased region so that the radiation is applied predominately to the diseased tissue and minimally to the surrounding healthy tissue.

An accurate and precise contour of the treated region (the planning target volume or PTV) incorporates the motion of the target during fractionated treatment. Since PTV's include an outline of the diseased tissue as well as a margin to account for patient setup and motion error, some healthy tissue will be exposed to the radiation. During the course of a radiotherapy treatment, a patient may receive fractionated treatment which may occur over an extended period of time. Movement of the diseased tissue and the surrounding healthy tissue over this time period is inevitable and increases the amount of healthy tissue that is exposed to radiation. Motion can be physical movement of the patient (setup error) or movement and deformation of the internal tissues, including the diseased tissue, caused by physiological functions, such as cardiac, respiratory, and digestive systems, or as a result of treatment response, such as reduction in tumor size.

Some motion, such as breathing and heart motion, can be accounted for through a combination of 4D imaging and respiratory gating or dynamic collimation to integrate the tumor motion into the treatment, thereby allowing the definition of the PTV to be improved. In addition, this information enables calculation of the true dose that was delivered over the course of treatment more accurately by quantifying the motion during a breathing cycle. However, the estimation of tumor motion requires the delineation of the tumor using manual outlining on two-dimensional slices or interactive segmentation tools. This process is too time intensive and lacks reproducibility. As such, there exists a need for a radiotherapy process that accurately, quickly and reliably accounts for motion during the course of a radiotherapy treatment.

The present invention is directed to a method and apparatus of accounting for tumor motion during radiation therapy treatment. Intra-fractional and inter-fractional motion affects the accuracy and precision of a radiation therapy plan. The method and apparatus disclosed herein provides for periodic updating of the radiation therapy plan to account movement of the tumors.

In one embodiment, radiation therapy planning images are acquired. A radiation therapy plan is developed from the radiation planning images. Fractionated radiation therapy treatments are then conducted. For those fractionated radiation therapy treatments that are based on updated radiation therapy plans, radiation therapy treatment images are acquired, automatically segmented and then subjected to deformable registration. This allows for a given fractionated radiation therapy treatment to be based on the current size and location of the tumor, and thus be delivered more precisely.

In the accompanying drawings, which are incorporated in and constitute a part of this specification, embodiments of the invention are illustrated, which, together with a general description of the invention given above, and the detailed description given below serve to illustrate the principles of this invention. One skilled in the art should realize that these illustrative embodiments are not meant to limit the invention, but merely provide examples incorporating the principles of the invention.

Figure 2:
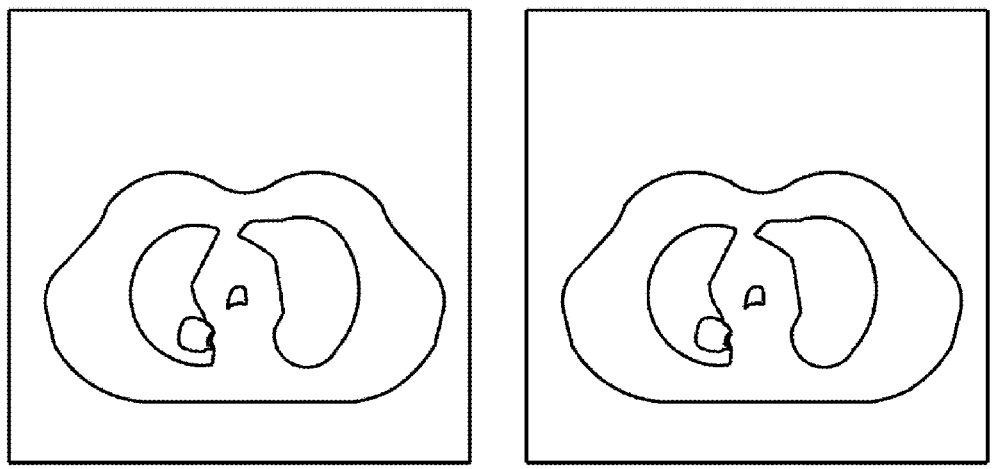
FIG. 2 illustrates segmented tumor and lungs in axial slices of two three-dimensional CT's taken at different phases of the breathing cycle.

The method for accounting for tumor movement in radiotherapy treatment disclosed herein provides for the automation of motion estimation of a tumor subject to the radiotherapy treatment. The method provides for automated segmentation of the tumor, which is then used in a registration algorithm to correlate similar points and account for movement. The method allows for an accurate, quick and reliable update of the PTV, which allows for an improved radiation treatment. By accounting for movement, such as that shown in FIG. 2, of the tumor and surrounding tissues during radiation treatment and in between fractionated radiation treatments, radiation plans can be updated to account for movement of the diseased tissue and surrounding organs at risk. An updated radiation therapy plan allows for more precise application of radiation to the desired target area and minimizes the exposure of healthy tissue to radiation.

In one embodiment of the method disclosed, a zero-click automation of tumor motion estimation is provided by using a deformable image registration algorithm in combination with an automated segmentation algorithm. It should be noted that any suitable combination of deformable registration and automated segmentation can be used. For example, the registration algorithm can be based on any deformable voxel-based registration method. In one particular embodiment, for example, the segmentation algorithm can be based on a method for automatic segmentation of lung nodules, and the registration method on a deformable B-spline or elastic body spline registration method. Such a registration method is described in "Medical Image Registration", V. Hajnal, D. Hill, D. Hawkes (editors), CRC Press, 2001, the entire disclosure of which is hereby incorporated by reference. An example of a suitable segmentation process is described in International Patent Application Publication No. WO2004046995A2, published in the name of Wiemker and Koninklijke Philips Electronics N.V and entitled "Computer-Aided Detection of Lung-Nodules," the entire disclosure of which is hereby incorporated by reference.

Figure 3:
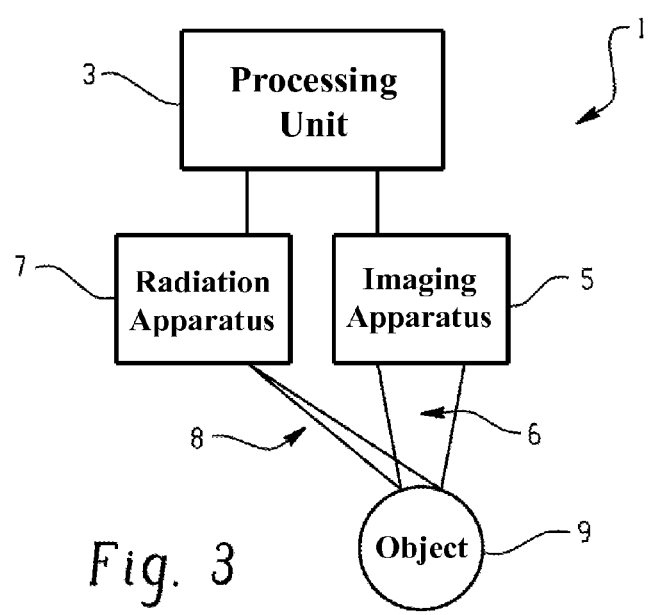
FIG. 3 illustrates a schematic of one embodiment of an apparatus that can account for tumor movement in radiotherapy treatment.

FIG. 3 illustrates one embodiment of an apparatus 1 that can account for tumor movement during radiation therapy. The apparatus 1 includes a processing unit 3 that is connected to an imaging apparatus 5 that takes an image 6 of object 9 and a radiation apparatus 7 that radiates object 9. One skilled in the art should appreciate that the imaging apparatus 5 and radiation apparatus 7 can be a variety of different apparatuses that provide an image of an object and that radiates an object, respectively. For example, the imaging apparatus can be a CT, MRI, ultrasound, SPECT/CT, PET/CT, x-ray, or other imaging device. The processing unit 3 can also take the form of a number of different units, provided the processing unit can perform the methods or processes described herein.

Figure 1:
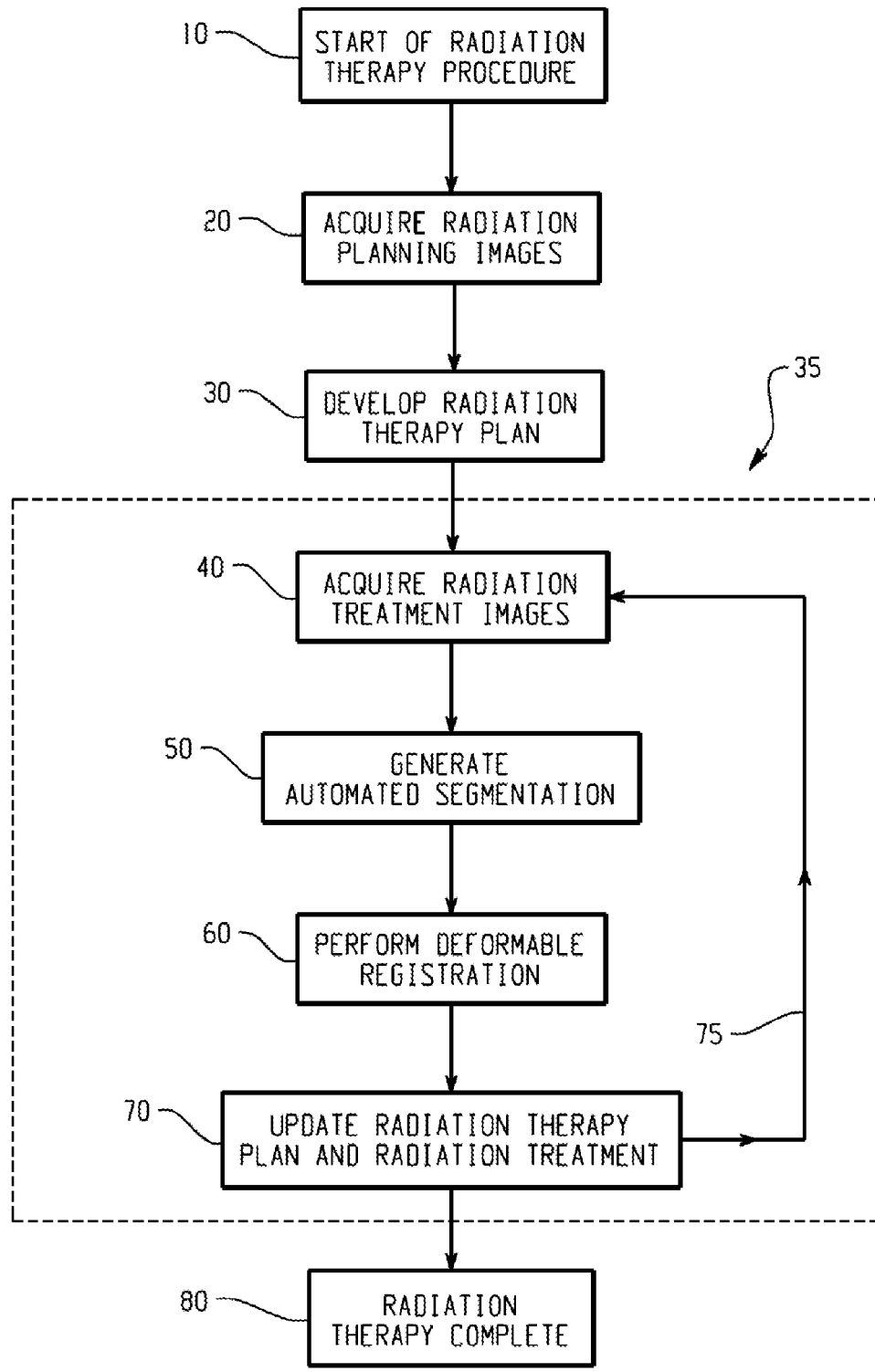
FIG. 1 illustrates a process flow chart for a method for accounting for tumor movement in radiotherapy treatment.

FIG. 1 illustrates one possible embodiment of a method for implementing a zero-click automation of tumor motion. The process begins at 10 and then radiation therapy planning images are taken at 20. At 30, a radiation therapy plan is developed from the radiation therapy planning images. The radiation therapy plan maps the contours of the tumor and, optionally, the surrounding organs and prescribes a radiation dose to the various contoured regions. This radiation therapy plan is implemented for the radiation therapy treatment shown at 35 in FIG. 1.

A radiation therapy treatment fraction is a fraction of the entire prescribed radiation dose. For example, a radiation therapy treatment might consist of 30 separate fractions, one fraction a day over the course of a month. In this regard, each radiation therapy fraction can be based on an updated radiation therapy plan, as described below. However, it should be appreciated that an updated radiation therapy plan might not be needed for each treatment. For example, an updated radiation therapy plan might be acquired for every other radiation therapy treatment, every third therapy treatment, or on some other regular or irregular interval basis. The interval in which an updated radiation treatment is acquired is dependent on the relative amount of movement of the tumor and organs at risk, and the degree of accuracy required in order to provide a successful treatment.

For a given radiation therapy treatment 35, radiation therapy treatment images are acquired at 40. The images are then automatically segmented at 50. The process then moves to 60 where a deformable registration is performed on the segmented images. The deformable registration allows for the contours of the imaged region to deform based on movement of the contoured regions. Movement of the contoured regions can result from movement of the patient, movement of the internal organs caused by physiological systems of patient, changed size of the contoured area, or a combination thereof. The deformed contoured regions of the imaged region allows for the radiation therapy plan to be updated based on the new, more accurate contoured regions. At 70, the radiation therapy plan is updated and a fractionate radiation therapy treatment occurs. If there are additional fractionated treatments in the radiation therapy treatment 35 the method loops 75 back to 40. If there are no additional fractionated radiation therapy treatments, the method proceeds to 80 where the radiation therapy treatment is complete.

The invention has been described with reference to one or more preferred embodiments. Clearly, modifications and alterations will occur to other upon a reading and understanding of this specification. It is intended to include all such modifications and alterations insofar as they come within the scope of the appended claims or equivalents thereof.

The invention claimed is:

1. A method of accounting for tumor movement during radiation therapy treatment comprising:
   (a) acquiring a radiation planning image;
   (b) developing a radiation therapy plan; and
   (c) performing a first set of fractionated radiation therapy treatments, each comprising:
      (i) acquiring radiation treatment images;
      (ii) generating an automated segmentation of the radiation treatment images;
      (iii) performing deformable registration of the segmented radiation treatment images;
      (iv) updating the radiation therapy plan based on the deformable registration of the segmented radiation treatment images; and
      (v) providing radiation treatment based on the updated radiation therapy plan.

2. The method of claim 1 further comprising performing a second set of fractionated radiation therapy treatments, each comprising providing radiation treatment based on a prior radiation therapy plan.

3. The method of claim 2, wherein said first set of fractionated radiation therapy treatments and said second set of fractionated radiation therapy treatments comprise a complete radiation therapy treatment.

4. The method of claim 2, wherein said first set of fractionated radiation therapy treatments and said second set of fractionated radiation therapy treatments are interdispersed during the course of a radiation therapy treatment.

5. The method of claim 4, wherein said first set of fractionated radiation therapy treatments and said second set of fractionated radiation therapy treatments are interdispersed in a set interval during the radiation therapy treatment.

6. The method of claim 1, wherein said automated segmentation of the radiation treatment images is based on a method for automatic segmentation of lung nodules.

7. The method of claim 1, wherein said deformable registration of the segmented radiation treatment images is based on a deformable B-spline or elastic body-spline registration method.

8. An apparatus for accounting for tumor movement during radiation therapy treatment comprising:
   (a) a means for acquiring a radiation planning image;
   (b) a means for developing a radiation therapy plan; and
   (c) a means for performing a first set of fractionate radiation therapy treatments, each comprising:
      (i) a means for acquiring radiation treatment images;
      (ii) a means for generating an automated segmentation of the radiation treatment images;
      (iii) a means for performing deformable registration of the segmented radiation treatment images;
      (iv) a means for updating the radiation therapy plan based on the deformable registration of the segmented radiation treatment images; and
      (v) a means for providing radiation treatment based on the updated radiation therapy plan.

9. The apparatus of claim 8 further comprising a means for a second set of fractionated radiation therapy treatments, each comprising a means for providing radiation treatment based on a prior radiation therapy plan.

10. The apparatus of claim 9, wherein said first set of fractionated radiation therapy treatments and said second set of fractionated radiation therapy treatments comprise a complete radiation therapy treatment.

11. The apparatus of claim 9, wherein said first set of fractionated radiation therapy treatments and said second set of fractionated radiation therapy treatments are interdispersed during the course of a radiation therapy treatment.

12. The apparatus of claim 11, wherein said first set of fractionated radiation therapy treatments and said second set of fractionated radiation therapy treatments are interdispersed in a set interval during the radiation therapy treatment.

13. The apparatus of claim 8, wherein said means for generating an automated segmentation of the radiation treatment images includes a means for segmentation based on a method for automatic segmentation of lung nodules.

14. The apparatus of claim 8, wherein said means for performing deformable registration of the segmented radiation treatment images includes means for registration based on a deformable voxel-based registration method.

15. A radiation therapy planning tool comprising:
a means for accepting radiation therapy planning images;
a means for contouring select regions of the radiation therapy planning images;
a means for assigning a radiation dose to each of the contoured regions within the therapy planning images;
a means for accepting radiation therapy treatment images;
a means for generating an automated segmentation of the radiation therapy treatment images;
a means for performing deformable registration of the segmented radiation therapy treatment images; and
a means for adjusting the contours of the select contoured regions based on the deformable registration of the segmented radiation therapy treatment.

* * * * *